US00PP37547P3

(12) United States Plant Patent
Elstgeest

(10) Patent No.: US PP37,547 P3
(45) Date of Patent: Jul. 28, 2026

(54) ***ALOCASIA* PLANT NAMED 'ELSTLALU'**

(50) Latin Name: *Alocasia cucullata*
Varietal Denomination: ELSTLALU

(71) Applicant: ELSTGEEST YOUNG PLANTS HOLDING B.V., Rijsenhout (NL)

(72) Inventor: Debbie Elstgeest, Rijsenhout (NL)

(73) Assignee: Elstgeest Young Plants Holding BV, Rijsenhout (NL)

( * ) Notice: Subject to any disclaimer, the term of this patent is extended or adjusted under 35 U.S.C. 154(b) by 0 days.

(21) Appl. No.: 19/346,972

(22) Filed: Oct. 1, 2025

(65) Prior Publication Data

US 2026/0157251 P1 Jun. 4, 2026

(30) Foreign Application Priority Data

Dec. 4, 2024 (QZ) ..... PBR 2024/3005

(51) Int. Cl.
*A01H 5/12* (2018.01)
*A01H 6/10* (2018.01)

(52) U.S. Cl.
USPC ..... Plt./373
CPC ..... *A01H 6/10* (2018.05); *A01H 5/12* (2013.01)

(58) Field of Classification Search
USPC ..... Plt./373
See application file for complete search history.

(56) References Cited

U.S. PATENT DOCUMENTS

PP26,607 P2 * 4/2016 Garner ..... A01H 6/10 Plt./373

* cited by examiner

*Primary Examiner* — Susan Mccormick Ewoldt
*Assistant Examiner* — Zachariah Allan Kay
(74) *Attorney, Agent, or Firm* — James R. Holm; Plant Novelty Rights, LLC

(57) ABSTRACT

A new and distinct *Alocasia* plant named 'ELSTLALU' particularly distinguished by a dark green background leaf coloration with irregular white to light green mottling and marbling, distinct mottled and marbled variegation distributed across most of the leaf surface, and a tall, upright growth habit with elongated petioles and an open appearance.

2 Drawing Sheets

Figure 1:
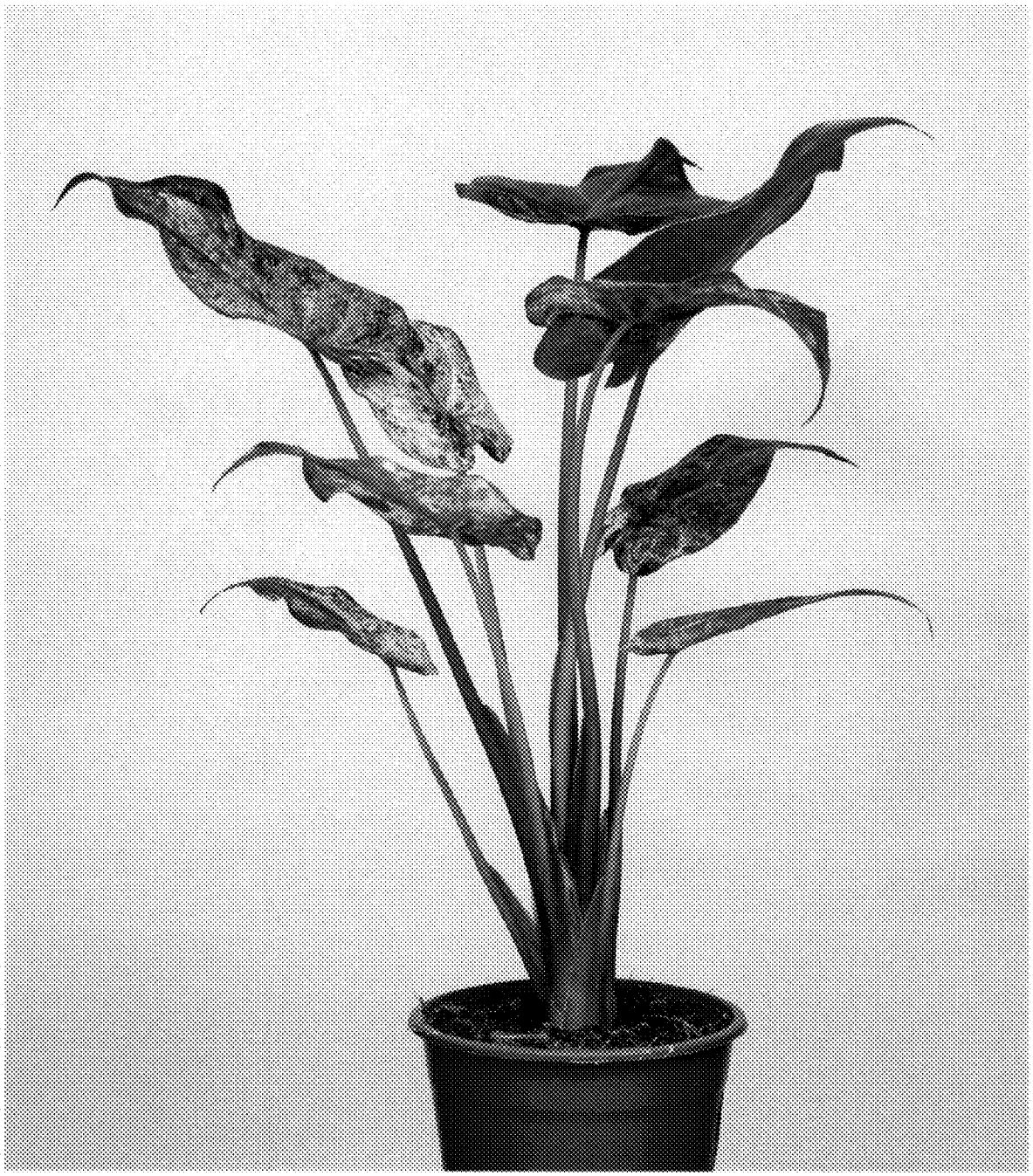

Genus and species: *Alocasia cucullata.*
Variety denomination: 'ELSTLALU'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date. This application claims priority to CPVO application no. 2024/3005 filed on Dec. 4, 2024.

BACKGROUND OF THE NEW PLANT

The present invention comprises a new and distinct variety of *Alocasia* plant, botanically known as *Alocasia cucullata*, and hereinafter referred to by the variety name 'ELSTLALU'. The new cultivar is a naturally occurring branch mutation originating from an unnamed and unpatented population of *Alocasia cucullata* plants cultivated in a greenhouse in Rijsenhout, The Netherlands. Several mutations were selected by the inventor from said population of *Alocasia cucullata* plants for a period of 4 months. The mutations were grown in 14 cm pots and observed for uniformity, stability, and distinctness as well as for their commercial potential. From amongst these mutations, 'ELSTLALU' was selected by the inventor in January 2022 for further propagation and commercialization based on its unique plant shape, the attractiveness of its foliage color, and unique growth habit.

The new *Alocasia* cultivar 'ELSTLALU' was first reproduced asexually using meristematic tissue culture in July 2022 in Rijsenhout, The Netherlands. Asexual propagation by meristematic tissue culture of the new variety has shown that the unique features of the new variety are stable and reproduced true-to-type to date through 10 successive generations.

SUMMARY OF THE INVENTION

The new *Alocasia* cultivar 'ELSTLALU' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'ELSTLALU' as a new and distinct variety of *Alocasia.*

1. *Alocasia* 'ELSTLALU' exhibits a dark green background leaf coloration with irregular white to light green mottling and marbling.
2. *Alocasia* 'ELSTLALU' exhibits a distinct mottled and marbled variegation distributed across most of the leaf surface.
3. *Alocasia* 'ELSTLALU' exhibits a tall, upright growth habit with elongated petioles and an open appearance.

The new *Alocasia* cultivar can be distinguished from its progenitor or parent species *Alocasia cucullata* by having variegated leaves and a more compact growth habit, whereas the parent *Alocasia cucullata* has solid green leaves with no variegation and a less compact growth habit.

DESCRIPTION OF THE PHOTOGRAPHS

This new *Alocasia* cultivar is illustrated by the accompanying-colored photographs which show the overall appearance and distinct characteristics of the plant. The colors shown are as true as can be reasonably obtained by conventional photographic procedures. The photographs are 20-week-old plants grown in 14-centimeter circular containers in a conventional glass greenhouse in Rijsenhout, The Netherlands. Colors in the photographs may differ slightly from the color values cited in the botanical description which accurately describes the colors of the new variety.

FIG. 1. shows the overall plant form and foliage of 'ELSTLALU'.

Figure 2:
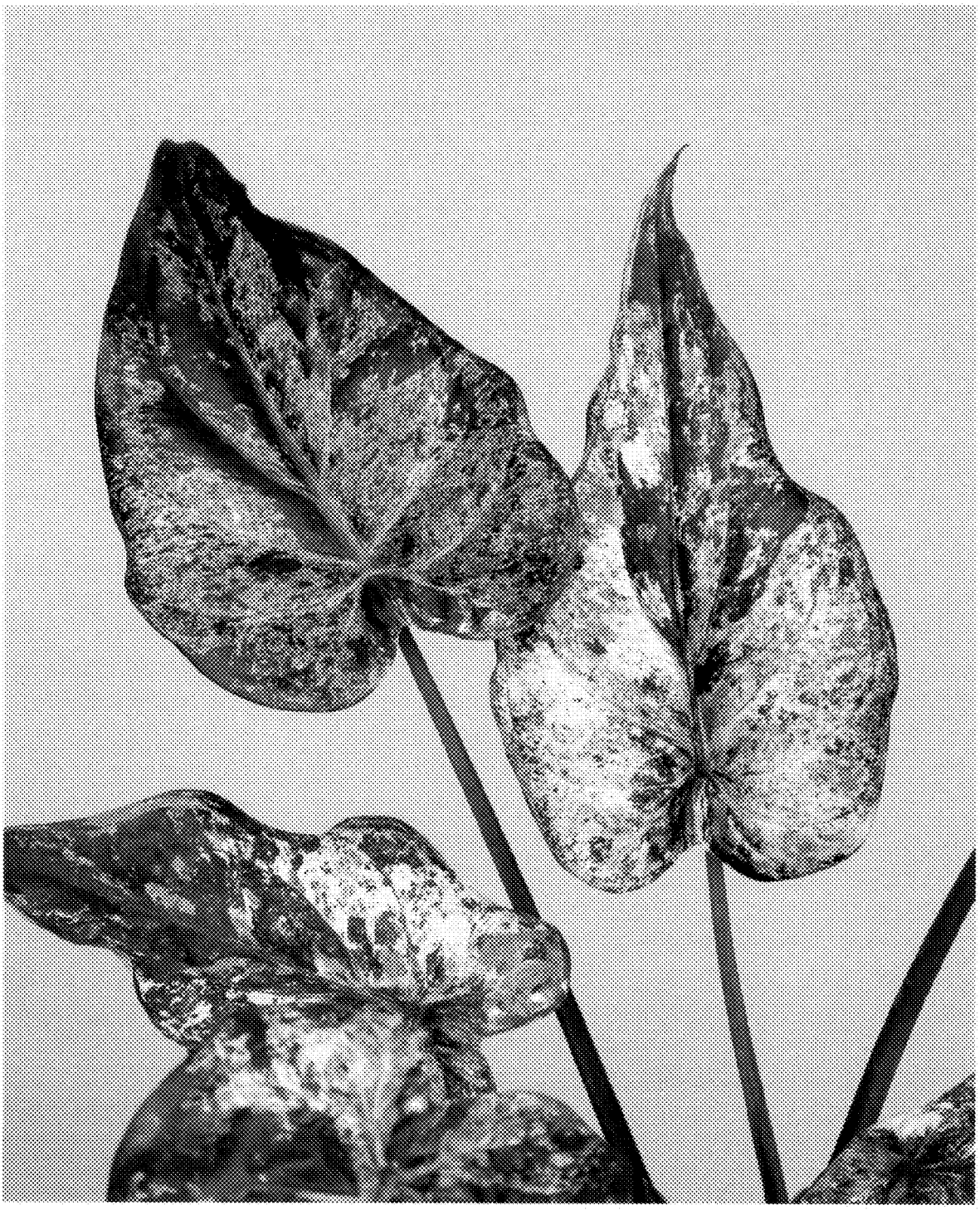

FIG. 2. shows a close-up of typical leaves of 'ELSTLALU'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional glass greenhouse located in Rijsenhout, The Netherlands. Growing condition consisted of an average day and night temperature of 20° C. to 22° C., 60 to 85 percent relative humidity, 150-200 μmol/m$^2$/sec (PAR) of light, and 600 to 700 ppm of CO2. Detailed descriptions were taken in November 2024 from 20-week-old plants grown in 14-centimeter circular containers. Measurements and numerical values represent averages of typical plant types.

DETAILED BOTANICAL DESCRIPTION

Classification:

*Family*.—Araceae.

*Botanical*.—*Alocasia cucullata*.

*Denomination*.—'ELSTLALU'.

General description:

*Plant type*.—Tropical perennial for use as a potted ornamental plant.

*Crop time*.—Approximately 20 weeks from propagation to a saleable plant.

*Approximate container size and/or cropping system*.—12.0 cm or larger pots.

*Growth habit*.—Broad and upright.

*Overall plant shape*.—Broad inverted triangular to obovate.

*Height from soil level to top of foliar plane*.—30.0 cm.

*Plant diameter or area of spread*.—38.5 cm.

*Growth rate*.—Moderate.

*Plant vigor*.—Moderate.

*Branching habit*.—Growth emerges from basal clumps.

*Stem description*.—Stemless.

*Quantity of divisions or clumps per plant*.—1.

*Propagation type*.—Meristematic tissue culture.

Foliage description:

*Arrangement*.—Alternate, simple.

*Quantity of leaves per basal clump*.—Average of 9.

*Lamina*.—Shape: Ovate to broad ovate, moderately elongated. Length: Average 18.6 cm. Width: Average 11.4 cm. Aspect: Flat to very slightly concave. Apex shape: Apiculate to aristate, pointed downwards at an average angle of 60° to the lamina. Base shape: Cordate to hastate. Margins: Entire, slightly repand, and slightly to moderately coarsely undulate. Texture (both upper and lower surfaces): Smooth, glabrous and moderately leathery. Pubescence: Not present. Luster: Upper surface: Very slightly glossy. Lower surface: Slightly glossy. Color: Juvenile foliage: Upper surface: Slightly darker than 143A (green) and sparsely and irregularly blotched and marbled with 147D (yellow-green). Lower surface: A blend of 143A and 146B (yellow-green) and sparsely and irregularly blotched and marbled with 147D (yellow-green). Mature foliage: Upper surface: A blend of 139A and 147A (green to yellow-green), and densely to very densely, irregularly finely dotted and marbled with 191A, 191B, and 193A (greyed green) and 157C and 157D (green-white). Lower surface: A blend of 147A and 147B (yellow-green), and densely to very densely, irregularly finely dotted and marbled with 191A, 191B, 193B, 193C (greyed green) and 157C and 157D (green-white). Venation: Pattern: Pinnate. Color (mature leaves): Upper surface: NN137A (green) and slightly to heavily axillary striped with 191A, 191B and 193A (greyed green) and 157C and 157D (green-white). Lower surface: 146C and 146D (yellow-green) and axillary striped with 146A (yellow-green).

*Petiole*.—Length: 29.8 cm. Diameter: 0.9 cm at the proximal end and 0.3 cm at the distal end. Texture: Smooth, glabrous. Luster (both upper and lower surfaces): Matte. Strength: Strong. Color: Upper surface: 137C (green) and radially striped with 137A (green). Lower surface: 137C and 137D (green) and radially striped with 137A (green). Wings: Length: Average 12.1 cm. Width: Average 1.1 cm. Color: Inner surface: 138B (green) and radially striped with 137B (green). Outer surface: 138A and 138B (green) and radially striped with 137B (green).

Inflorescence: None observed to date.

High temperature tolerance: Up to 40 degrees Celsius.

Low temperature tolerance: Greater than 5 degrees Celsius.

USDA hardiness zones: Zones 10 to 13.

Rain tolerance: Moderate to high.

Wind tolerance: Low.

Disease and pest tolerance: No claims are made to any superior disease or insect resistance or tolerance.

COMPARISON WITH RELATED KNOWN VARIETY

The new *Alocasia* cultivar 'ELSTLALU' can be distinguished from the related known variety of *Alocasia cucullata* 'Variegata' (unpatented) in the following characteristics described in Table 1 below.

TABLE 1

| Characteristic | 'ELSTLALU' | 'Variegata' |
|---|---|---|
| Leaf shape. | Ovate to broad ovate, moderately elongated. | Broadly triangular to heart-shaped, less elongated. |
| Leaf color (upper surface). | Dark green background with irregular white to light green mottling and marbling. | Bright chartreuse to light green with darker green sectorial variegation near the margins. |
| Leaf pattern. | Distinct mottled and marbled variegation distributed across most of the leaf surface. | Predominantly solid bright green with occasional contrasting patches. |
| Leaf size. | Larger, typically 18-25 cm in length. | Smaller, typically 10-15 cm in length. |
| Leaf orientation | Erect to outwardly arching. | More upright and slightly forward-facing. |
| Petiole color. | Green, sometimes with lighter striations. | Uniform light green. |
| Growth habit. | Taller, more upright with elongated petioles and a more open appearance. | Compact, shorter internodes, denser foliage. |

What is claimed is:

1. A new and distinct cultivar of *Alocasia* plant named 'ELSTLALU', substantially as illustrated and described herein.

* * * * *